(12) United States Patent
Haas

(10) Patent No.: US 8,252,602 B2
(45) Date of Patent: Aug. 28, 2012

(54) SYSTEM FOR EXPLOSIVES DETECTION

(76) Inventor: Jeffrey S. Haas, San Ramon, CA (US)

(*) Notice: Subject to any disclaimer, the term of this patent is extended or adjusted under 35 U.S.C. 154(b) by 1090 days.

(21) Appl. No.: 10/703,303

(22) Filed: Nov. 7, 2003

(65) Prior Publication Data

US 2005/0101027 A1    May 12, 2005

(51) Int. Cl.
*G01N 33/00*    (2006.01)

(52) U.S. Cl. ........ 436/169; 422/400; 422/401; 422/402; 422/68.1

(58) Field of Classification Search ........... 422/50, 422/55, 56, 5.7, 58, 99, 102, 104, 400, 401, 422/402, 68.1; 436/169
See application file for complete search history.

(56) References Cited

U.S. PATENT DOCUMENTS

| | | | | |
|---|---|---|---|---|
| 4,496,520 A * | 1/1985 | Heller et al. | ..................... | 422/60 |
| 4,788,039 A * | 11/1988 | Glattstein | ..................... | 422/61 |
| 5,035,860 A * | 7/1991 | Kleingeld et al. | ............ | 422/413 |
| 5,035,862 A * | 7/1991 | Dietze et al. | ................. | 422/68.1 |
| 5,138,889 A * | 8/1992 | Conrad | ..................... | 73/863.12 |
| 5,648,047 A * | 7/1997 | Kardish et al. | ................... | 422/56 |
| 6,077,711 A * | 6/2000 | Singer | ............................. | 436/66 |
| 6,228,657 B1 * | 5/2001 | Genovese et al. | ............ | 436/167 |
| 2004/0265169 A1 | 12/2004 | Haas et al. | | |
| 2005/0287036 A1 * | 12/2005 | Eckels et al. | .................... | 422/61 |

FOREIGN PATENT DOCUMENTS

WO    WO 2005/005962    1/2005

OTHER PUBLICATIONS

Pat Grant, Chemistry Field Assets, Presentation, Aug. 26, 2002, Albaquerque, NM, USA.
Brian Anderson, Jeff Haas, et al., Inovations for Detection of Propellout, et cet, May 15, 2000, Idaho, USA.
R.G. Parker, et al., Analysis of Explosives and Explosive Residues, 1975, Journal of Forensic Science.
R. W. Hiley, Investigations of Thin Layer Chromatographic Techniques, et cet, Jan. 5, 1993, England.
Jehuda Yinon & Shmuel Zitrin, The analysis of Explosives, Pergamon Press.
Hsien-Hui Meng & Brian Caddy, Gunshot Residue Analysis, Journal of Forensic Science, 1977.
J.M.F. Douse & R. N. Smith, Trace Analysis of Explosives, et cet, Journal of Energetic Materials, 1986.
Thomas F. Jenkins, et al., Development of Field Screening Methods, et cet, Talanta, vol. 39, Great Britain.

(Continued)

*Primary Examiner* — Sam P Siefke
(74) *Attorney, Agent, or Firm* — Dennis W. Beech

(57) ABSTRACT

The system and method for explosives detection may be used for detecting the presence of explosive elements. A testing device may have a case with a cover. A sample holder may be disposed in the case for receipt of a sample element and may have a sample retainer. The sample element may have a swipe pad attached to a backing element a heater may be disposed in the sample holder wherein the heater may be below the swipe pad adjacent the backing element when the sample element may be positioned in the sample holder. The heater may be in communication with an electric power source. The case may have a plurality of cavities formed therein for receipt of a plurality of fluid containers. The plurality of fluid containers may have at least a first reagent fluid and a second reagent fluid.

18 Claims, 2 Drawing Sheets

OTHER PUBLICATIONS

Sae-Im Nam, et al., On-Site Analysis of Explosives in the Soil, et cet, AEL 2000, CRREL-DOD, Aug. 1997.
Jay B. Fox, Jr., Kinetics and Mechanisms of the Griess Reaction, American Chemical Society, Aug. 1979.
Thomas F. Jenkins, et al., On-Site Analysis for High Concentrations of Explosives, et cet, CRREL-DOD, May 1996.
A.B. Crockett, et al., Field Sampling and Sellecting On-Site, et cet, U.S. EPA/540/R-97/501, Nov. 1996.
Alan B. Crockett, et al., Field Sampling and Selecting On-Site, et cet, U.S. EPA/540/S-97/501, Dec. 1996.
John I. Thornton, The Chemistry of Death by Gunshot, Analytica Chimica Acta, 1994, Amsterdam, Netherlands.
Rukmani Krishna Murthy, Simultaneous Detection of High Explosives, et cet, Journal of Planar Chromatograph, Sep./Oct. 1999.
Ronald P. Mamginell, et al., Finite Element Modeling of a Microhotplate, et cet, MEMs 99 Conference, Puerto Rico.
S.A. Peak, A Thin-Layer Chromatographic Procedure, et cet, Journal of Forensic Science, Jul. 1980.
Alexander Beveridge, Forensic Investigation of Explosives, Taylor & Francis Pub, 1993, United Kingdom.
Field Sampling and Selectign On-Site Analytical Methods for Explosives in Soil, Alan B. Crockett, et al., EPA/540/S-97/501, dated Nov. 1996.
Same title and author as "AS", dated Dec. 1996.

* cited by examiner

SYSTEM FOR EXPLOSIVES DETECTION

BACKGROUND OF THE INVENTION

This invention relates to systems and methods for detecting the presence of explosives and explosives residue. The new system and method may provide a compact test unit that incorporates a test method that may allow testing of sample articles at a selected location. The detection unit may use chemicals and other elements that reduce the hazard to a user.

Chemical detection of the presence of explosives and explosive residue has been known for many years. The methods and chemicals used in the past have tended to be cumbersome to transport and put into use at a selected site or location and the testing may have been time consuming. Special testing devices and apparatus may have been developed for specific explosives, but they may have been unreliable, dangerous to the user due to the chemicals used, or otherwise limited in identifying an explosives contaminated site or object.

A previously used chemical explosives identification technique that may have been reasonably reliable is thin layer chromatography or TLC. Testing apparatus and methods have been developed including kits for on-site testing. The calorimetric devices and methods including those using a TLC plate may have shortcomings for effective, efficient testing, e.g., difficulty of use, length of time, solvent waste disposal, use of toxic chemicals, large work area, need for calibration, limited type or number of explosive compounds detectable, use of glass as well as other issues.

The use of calorimetric testing or spot tests may have been recognized for many years as chemical reagents and methods were identified to detect the presence of a particular explosive. The calorimetric tests may afford quick results, may be easy to perform and may be sensitive relative to the explosive sample content, but may be limited in the number of different explosives detected. The most common spot test method may be to react explosives with a base, then allow time or heat the sample, than perform a Griess reaction test, and then allow more time or heat the sample. Various formulations of the Griess reagent may have been developed. Also numerous types of substrates, sorbant materials or swipes, such as, wool, cotton, polyfabrics, porcelain spot plates, TLC plates, curvettes, beakers, jars and the like may have been used to perform testing. All of these testing devices and methods may have been limited in the past as discussed above making them cumbersome and unwieldy to use and thereby limiting the flexibility necessary for quick, site selected and timely testing for detection of the presence of explosives or explosive residue.

SUMMARY OF THE INVENTION

The present invention is directed to devices for detecting the presence of explosive elements. A testing device may have a case with a cover. A sample holder may be disposed in the case for receipt of a sample element and may have a sample retainer. The sample element may have a swipe pad attached to a backing element. A heater may be disposed in the sample holder wherein the heater may be below the swipe pad adjacent the backing element when the sample element may be positioned in the sample holder. The heater may be in communication with an electric power source. The case may have a plurality of cavities formed therein for receipt of a plurality of fluid containers. The plurality of fluid containers may have at least a first reagent fluid and a second reagent fluid.

These and other features, aspects and advantages of the present invention will become better understood with reference to the following drawings, description and claims.

DETAILED DESCRIPTION

The following detailed description includes the best currently contemplated modes for carrying out the invention. The description is not to be taken in a limiting sense, but is made merely for the purpose of illustrating the general principles of the invention.

Figure 4:
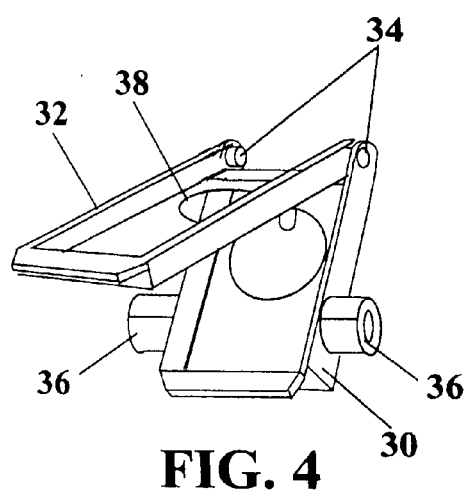
FIG. 4 illustrates a perspective view of the sample holder according to an embodiment of the invention.
Figure 1:
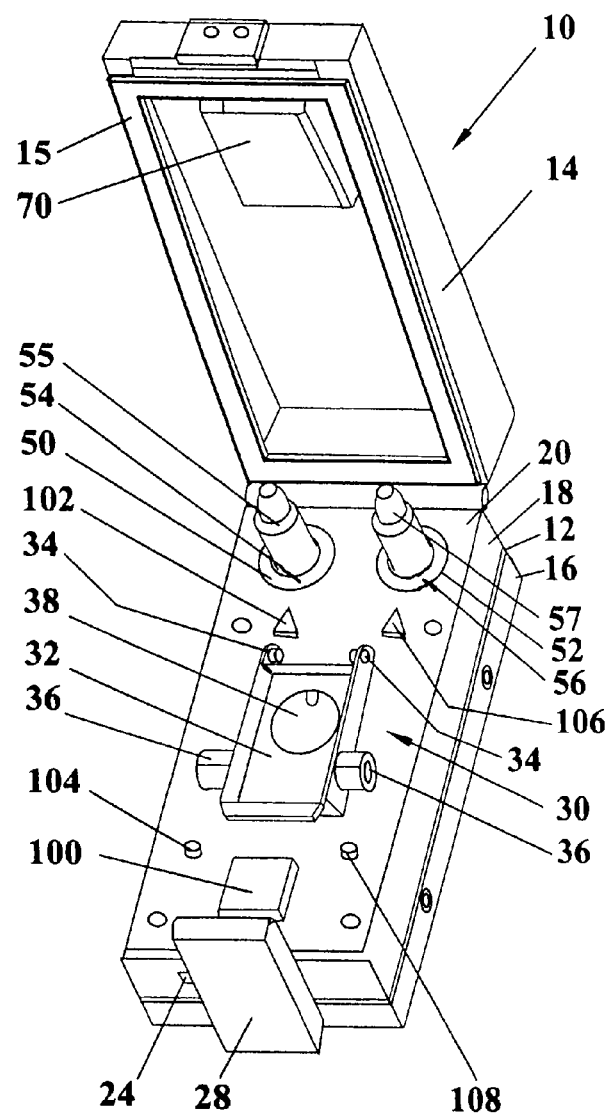
FIG. 1 illustrates a perspective view of a testing device according to an embodiment of the invention.
Figure 3:
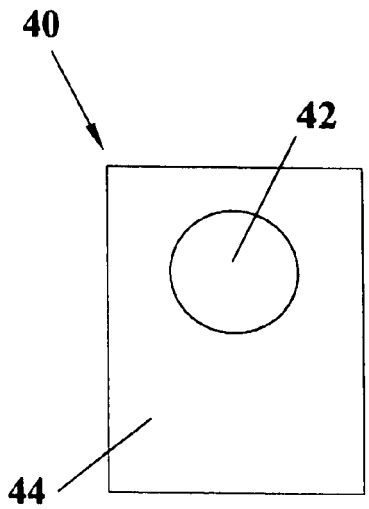
FIG. 3 illustrates a plan view of the sample element according to an embodiment of the invention.
Figure 3A:
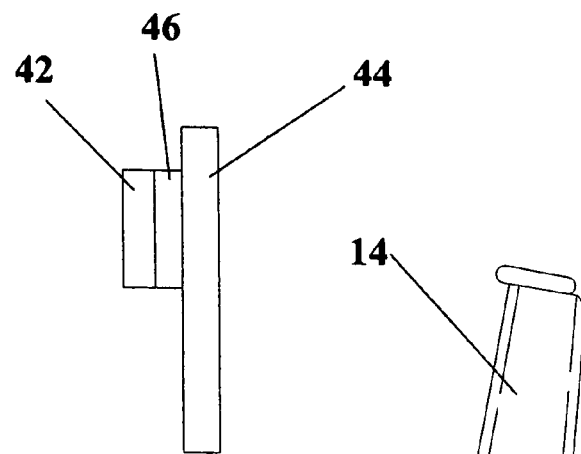
FIG. 3A illustrates a side view of the sample element according to an embodiment of the invention.
Figure 2:
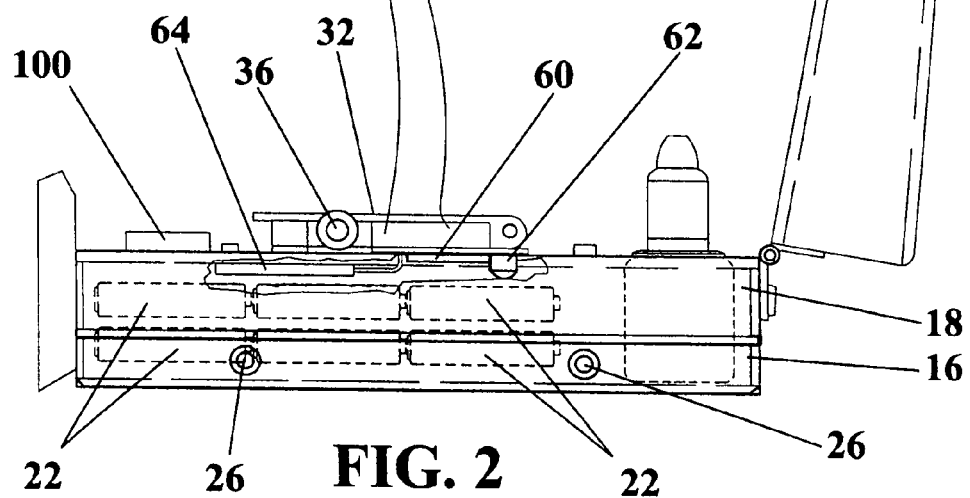
FIG. 2 illustrates a side elevation view of a testing device according to an embodiment of the invention.

Referring to FIGS. 1 and 2, a calorimetric testing device 10 for various types of explosives and related energetic decomposition products, for example, nitro-, nitrato-, and nitramine-type explosives and other yet untested compositions may have a case 12 and cover 14 and may be easy to transport to a selected location for testing. Cover 14 may have storage bin 70 for retaining extra swipes or swabs. The test device 10 may allow testing of explosive samples as low as a few nanograms to saturated milligram levels on a substrate swipe. Cover 14 or case 12 may be fitted with an O-ring or gasket 15 to seal against moisture or dirt. There may be a case latch 28 for retaining the closed cover 14 to the case 12.

The case 12 may have a bottom 16 assembled with an enclosure 18 having an upper panel 20. There may be enclosure attachments 26 such as screws, bolts, quick release devices or the like for access to the batteries 22. The case 12 and cover 14 may be hinged or otherwise attached. Batteries 22 may be disposed in the case 12 with a power switch 24 positioned on the case 12 and a power on/off indicator 108. There may be a sample holder 30 attached to the upper panel 20 that may have a heater 60 disposed therein. The heater 60 may be in communication with said batteries 22 and a temperature sensor 62. There may also be a voltage regulator 64 to allow use of an external power source.

Referring to FIGS. 1 through 4, there may be a sample retainer 32 attached by a hinge 34 to hold a sample element 40 or swipe. The sample retainer 32 may have a retainer aperture 38 and may be held in place by spring ball retainers 36. The sample element 40 may have a swipe pad 42 attached by pad attachment 46 to a backing element 44. The swipe pad 42 may be attached by adhesive, glue or other suitable element that maintains attachment and environment integrity up to approximately 150° C. without decomposing or other damage. The swipe pad 42 may be a defined size such as circular with an approximate diameter of 0.75 inches to accommodate test sample sizes and not require excessive use of reagent fluid. The pad attachment 46 may be chemically resistant and non-porous to inhibit the absorption of reagent fluid. The pad attachment, if for example adhesive, may also be of white color to not interfere with the visual evaluation of the swipe pad 42 during testing. If the pad attachment 46 is not positioned under the swipe pad 42, the backing element may be white colored in the area of the swipe pad 42. The pad attachment 46 may also be selected to minimize interference in heating swipe pad 42.

The swipe pad 42 may be formed of material that may be resistant to chemical degradation during testing in the approximate pH range of 1 through 14 to avoid reacting or decomposing. The swipe pad 42 may be white in color to aid test evaluation, may be heat resistant up to approximately 150° C. and may have hydrophilic properties for wetting using fluid reagents. The swipe pad 42 may also be roughened, for example, by use of a woven material, to aid in retrieving test sample particles from the environment. The swipe pad 42 may also be thick enough to resist damage such as tearing during sampling, yet not be to thick such that heating of the test sample is inhibited. When the sample element 40 may be positioned in the sample holder 30, the swipe pad 42 may be disposed relative to the retainer aperture 38.

Any geometric shape of swipe pad 42 may be used; however, a circular swipe pad 42 may provide for even wicking to the outer edges avoiding the occurrence of unwetted corners. It has been found by experiment that a swipe pad 42 circular shape with approximately 0.75 inch diameter and 0.002 inch to 0.005 inch thickness may allow an adequate test sample size of material to be wetted with a minimum use of reagent fluid. With a woven 100% continuous filament virgin polyester material, approximately 50 microliters of reagent may be sufficient for testing. Selecting swipe pad 42 characteristics may provide adequate surface area to perform the test sample collection or swiping task and reduce the volume of reagent necessary for transport with the testing device 10.

The backing element 44 may support the swipe pad 42 when in use for example to collect test samples. It may also protect the swipe pad 42 from contamination due to handling and may protect the swipe pad 42 from the heater 60. It has been found by experiment that a polyester material such as MYLAR may be used for the backing element 44. The polyester material may be resistant to chemical degradation and it may facilitate heat transfer to the swipe pad 42 without decomposing due to heating. The polyester material may be white in color to aid in test evaluation.

There may be a pair of cavities 50, 52 for positioning fluid containers 54, 56 in the case 12. The fluid container 54 may have cap 55 and the fluid container 56 may have cap 57. The fluid containers 54, 56 may have a reagent for use in testing a test sample for the presence of explosives or residues thereof. The fluid containers 54, 56 may be one of various types, for example, squeeze to release a drop of fluid, have a dropper incorporated in the cap, have a pump or pump type cap to move fluid, or other fluid extraction method or structure.

Tetrabutylammonium hydroxide may be used in a reagent test to impart a color to nitroaromatic compounds that may otherwise not be detected by other bases, such as, sodium hydroxide or potassium hydroxide regardless of their respective concentrations. The tetrabutylammonium hydroxide may also be strong enough to create nitrite salts for other types of explosives that may be in the test sample in preparation for testing with a second type reagent. Use of tetrabutylammonium hydroxide may be difficult due to limited shelf life and its reaction to environmental carbon dioxide that may degrade the necessary color chemistry with nitroaromatics. To develop a solvent system mixable with water to inhibit degradation and reduce hazardous effects to a user, an ethanol and water mixture may be used to inhibit tetrabutylammonium hydroxide degradation with the ethanol ratio such as not to be flammable. The ethanol and water may also have minimum nitrite content to avoid reaction to a second type reagent test that may give false positive results. For example, if a 10 nanogram detection threshold may be used any nitrite content in the solutions may be less than 0.2 nanograms per microliter of fluid to minimize corruption of test results or false detection.

The first reagent test may use a first reagent fluid that may have an optimum detection performance range with the fluid having a tetrabutylammonium hydroxide in a water solution in the approximate range of 0.7 to 0.9 Molar and an ethanol as approximately 35 percent of the water solution. Test results may be obtained using a wider tolerance of elements in the first reagent fluid, but there may be reduced detection sensitively. The tetrabutylammonium hydroxide in water solution may be in the approximate range of 0.1 to 1.53 Molar and the ethanol as approximately 5 to 95 percent of the water solution. Also, other alcohols or blends of alcohols may be used in place of ethanol; however, for example, methanol may be toxic to the user and isopropyl may be less toxic, but may have poorer detection sensitivity results and cause shorter shelf life for the reagent fluid.

A second reagent test may be a Griess reagent test. The Griess reagent may cause a highly colored azo dye to be created in a reaction with nitrite salts. The acid that may be used in the formulation of the second reagent may be phosphoric acid that may reduce hazardous effects to a user that may become a buffer during the reaction thereby buffering against itself to inhibit creation of too much acid on the swipe pad 42. Other types of acids that may be used in the Griess test may react too violently with the base, may be toxic or hazardous, or may create a strong odor.

The phosphoric acid may be mixed with sulfanilic acid and N-(1-naphthyl) ethylenediamine dihydrochloride. The sulfanilic acid may be water soluble with reduced toxicity and it may impart a deep magenta color to the test sample for ease of detection of explosives. N-(1-naphthyl) ethylenediamine dihydrochloride may be water soluble and not carcinogenic as with other salts, and may impart an effective color reaction from the test sample. The second reagent solution may use deionized water that may have minimum nitrite content to reduce false positive test results. For example, if a 10 nanogram detection threshold may be used any nitrite content in the solutions may be less than 0.2 nanograms per microliter of fluid to minimize corruption of test results or false detection.

The second reagent test may use a second reagent fluid that may have an optimum detection performance range with the fluid having a phosphoric acid in a water solution in the approximate range of 1.3 to 1.7 Molar; and a sulfanilic acid of approximately 8 grams with a N-(1-naphthyl) ethylenediamine dihydrochloride of approximately 5 grams per 1000 milliliters of the phosphoric acid in water solution. Test results may be obtained using a wider tolerance of elements in the second reagent fluid, but there may be reduced detection sensitivity. The phosphoric acid in water solution may be in the approximate range of 0.1 to 7.35 Molar, the sulfanilic acid may be in the approximate range of 5 to 8 grams, and the N-(1-naphthyl) ethylenediamine dihydrochloride may be in the approximate range of 5 to 9 grams. Other acids, acid combinations, or acid concentrations may be used, but may produce less than optimal testing sensitivity results. Other solutions may have increased acidity and be hazardous to the user as well as have a detrimental effect on the testing device. Other solutions may not be acidic enough for a detection reaction to occur or may be toxic. Other salts may be used, but they may reduce the explosives detection sensitivity.

There may be indicators and a mode switch 100 for use in facilitating the testing of a test sample. An example configuration may be described in an example test method that may be used to test for explosives and related energetic decomposition products as follow.

A user may take a sample element 40 and swipe an object to be evaluated to obtain a test sample on the swipe pad 42. The sample element 40 may then be placed in the sample holder 30 and retained by the sample retainer 32. This action may activate a green LED arrow 102 to signal the user to add a first reagent in fluid container 54 to the swipe pad 42. When the first reagent may be added the user may activate the mode switch 100 that may deactivate the green LED arrow 102 and activate the heater 60 as well as a green LED 104.

The heater 60 may heat to a temperature of approximately 150° C. in approximately 30 seconds. The heater 60 may then deactivate and the green LED 104 may be deactivated and a green LED arrow 106 may be activated to signal the user to add a second reagent in fluid container 56 to the swipe pad 42. When the second reagent may be added the user may lift the sample retainer 32 to remove the tested sample element 40 deactivating the green LED arrow 106.

During the test method described above, if there is a color change in the test sample after the first reagent in fluid container 54 may be applied, after the heating of the test sample or after the addition of the second reagent, there may be explosive material in the test sample.

While the invention has been particularly shown and described with respect to the illustrated embodiments thereof, it will be understood by those skilled in the art that the foregoing and other changes in form and details may be made therein without departing from the spirit and scope of the invention.

I claim:

1. A system for detecting the presence of explosive elements comprising:
   a testing device having a case with a cover;
   a sample holder disposed in said case for receipt of a sample element and having a sample retainer;
   said sample element comprising a swipe pad attached to a backing element wherein said swipe pad is approximately a circular shape, constructed of a woven continuous filament polyester material, is constructed of a roughened material that is resistant to chemical degradation for the entire pH range of approximately 1 to 14, is heat resistant for the entire temperature range of approximately 0 degrees C. to 150 degrees C., and is hydrophilic for each of a first reagent fluid and a second reagent fluid;
   a heater disposed in said sample holder wherein said heater will be below said swipe pad adjacent said backing element when said sample element is positioned in said sample holder wherein said heater is a variable control heater for the entire temperature range from ambient to approximately 150 degrees C.;
   said heater in communication with an electric power source;
   said case having a plurality of cavities formed therein for removable storage of a plurality of fluid containers; and
   said plurality of fluid containers is two fluid containers wherein a first fluid container has a first reagent fluid of a tetrabutylammonium hydroxide, an ethanol and a water, and a second fluid container has a second reagent fluid of a phosphoric acid, a sulfanilic acid, N-(1-naphthyl) ethylenediamine dihydrochloride and a water.

2. The system as in claim 1 wherein said heater may be raised in temperature from ambient to approximately 150° C. in 30 seconds time.

3. The system as in claim 1 wherein said swipe pad is a diameter of approximately 0.75 inches and a thickness between approximately 0.002 inches to 0.005 inches.

4. The system as in claim 1 wherein said swipe pad is constructed of a roughened material that is resistant to degradation for each of said reagent fluids for the entire pH range of approximately 1 to 14.

5. The system as in claim 1 wherein said roughened material is a woven fiber material that is white in color.

6. The system as in claim 1 wherein said plurality of fluid containers each having a fluid dispensing apparatus.

7. The system as in claim 6 wherein said fluid dispensing apparatus includes a pump.

8. The system as in claim 1 wherein said plurality of fluid containers each having a closure for opening to dispense a reagent fluid from said fluid container.

9. The system as in claim 1 wherein said first reagent fluid comprising:
   a tetrabutylammonium hydroxide in a water solution, from 0.1 to 1.53 Molar; and
   an ethanol, from 5 to 95 percent of said water solution.

10. The system as in claim 1 wherein said first reagent fluid comprising:
    a tetrabutylammonium hydroxide in a water solution, from 0.5 to 1.5 Molar; and
    an ethanol, from 25 to 50 percent of said water solution.

11. The system as in claim 1 wherein said first reagent fluid comprising:
    a tetrabutylammonium hydroxide in a water solution, from 0.7 to 0.9 Molar; and
    an ethanol as 35 percent of said water solution.

12. The system as in claim 1 wherein said second reagent fluid comprising;
    a phosphoric acid in a water solution, from 0.1 to 7.35 Molar; and
    a sulfanilic acid of 8 grams and an N-(1-naphthyl) ethylenediamine dihydrochloride of 5 grams per 1000 milliliters of said phosphoric acid in said water solution.

13. The system as in claim 1 wherein said second reagent fluid comprising:
    a phosphoric acid in a water solution, from 0.5 to 2.5 Molar; and
    a sulfanilic acid of 8 grams and an N-(1-naphthyl) ethylenediamine dihydrochloride of 5 grams per 1000 milliliters of said phosphoric acid in said water solution.

14. The system as in claim 1 wherein said second reagent fluid comprising:
    a phosphoric acid in a water solution, from 1.3 to 1.7 Molar; and
    a sulfanilic acid of 8 grams and an N-(1-naphthyl) ethylenediamine dihydrochloride of 5 grams per 1000 milliliters of said phosphoric acid in said water solution.

15. The system as in claim 1 wherein said first reagent fluid having less than 0.2 nanogram of a nitrite per microliter of fluid.

16. The system as in claim 1 wherein said second reagent fluid having less than 0.2 nanogram of a nitrate per microliter of fluid.

17. The system as in claim 1 wherein said swipe pad has an approximately circular shape of approximately 0.75 inch diameter and an approximate thickness of 0.002 to 0.005 inches.

18. The system as in claim 1 wherein said swipe pad is formed of a woven approximately 100 percent continuous filament virgin polyester material.

* * * * *